(12) United States Patent
Isozaki et al.

(10) Patent No.: US 6,654,111 B2
(45) Date of Patent: *Nov. 25, 2003

(54) SURFACE INSPECTION APPARATUS AND METHOD

(75) Inventors: Hisashi Isozaki, Tokyo (JP); Hiroshi Yoshikawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/789,699

(22) Filed: Feb. 22, 2001

(65) Prior Publication Data

US 2001/0035951 A1 Nov. 1, 2001

(30) Foreign Application Priority Data

Feb. 24, 2000 (JP) ........................................ 2000-047949

(51) Int. Cl.[7] .............................................. G01N 21/00
(52) U.S. Cl. ................................................... 356/237.3
(58) Field of Search ......................... 356/237.1–237.6, 356/238.1–238.3, 239.1–239.8, 338, 521, 492, 364, 367–369, 339, 613, 430–431; 250/559.09–559.18, 559.41–559.48, 306–307, 234, 310, 220–226, 223 R, 559.24, 548

(56) References Cited

U.S. PATENT DOCUMENTS

| | | | | |
|---|---|---|---|---|
| 6,104,481 A | * | 8/2000 | Sekine et al. | 356/237.2 |
| 6,169,601 B1 | * | 1/2001 | Eremin et al. | 356/237.1 |
| 6,191,849 B1 | * | 2/2001 | Maeshima et al. | 356/237.1 |

* cited by examiner

Primary Examiner—Tu T. Nguyen
(74) Attorney, Agent, or Firm—Foley & Lardner

(57) ABSTRACT

A first light receiving section and a second light receiving section receive light from an inspected object, and respectively form a first light receiving signal and a second light receiving signal which are different in sensitivity or dynamic range from each other. The first light receiving signal and the second light receiving signal which are different in sensitivity or dynamic range from each other are synthesized in order to form a measuring signal. The measuring signal is used to detect whether there are any foreign matters on a surface of the inspected object.

24 Claims, 14 Drawing Sheets

SURFACE INSPECTION APPARATUS AND METHOD

FIELD OF THE INVENTION

The present invention relates to a surface inspection method and apparatus for detecting various foreign matters on the surface of an inspected object.

PRIOR ART

A method has been heretofore known which enlarges a dynamic range, in a system in which detection light is incident on the surface of an inspected object to detect scattered light from foreign matter on the surface of an inspected object.

However, in the conventional detection system, the scattered light from the foreign matter is processed by one and the same processing system to secure the dynamic range of data. The scattered light from the foreign matter has not been utilized for the enlargement of continuous dynamic range due to the difference of detection object between data different in the processing system.

Further, a method for enlarging a dynamic range by software processing has been also known, but detection accuracy of sizes of foreign matter is poor as compared with the case where actual scattered light is captured.

Lately, with the progress of complicatedness and fineness of steps, it has been desired that smaller foreign matter and larger foreign matter can be measured simultaneously. The size of foreign matter on the surface of an inspected object to be measured includes a materially small size, and it is important to capture fine foreign matter with higher sensitivity.

It is necessary to grasp the more accurate size of foreign matter due to the necessity of analysis of foreign matter.

Further, it is necessary not only to measure only foreign matter but to grasp various information on the surface of an inspected object.

A wide dynamic range from small foreign matter to the rugged parts on the large surface has been obtained.

In the past, a detection device is sometimes arranged for the entirely different object in order to obtain various surface information.

However, the respective detection devices are not used for the object other than that of theirs, and are present merely for one function.

Further, in data obtained from the processing systems different from each other for processing the detection devices, even if the wide dynamic range can be achieved, data has been never prepared on the basis of foreign mater information from the high sensitivity side that sometimes includes saturated data. Therefore, the detection systems different from each other merely separately provide results. That is, there has not been proposed a widely continuous dynamic range that succeeded data from the high sensitivity side that sometimes contains saturated data.

SUMMARY OF THE INVENTION

An object of the present invention is to enable detection of various foreign matters on the surface of an inspected object with a wide dynamic range.

The present invention provides a surface inspection method and apparatus for detecting various foreign matters on the surface of an inspected object with a wide dynamic range, particularly, a widely continuous dynamic range.

In the past, since various data detected and processed by a plurality of detection systems which are different in magnification and sensitivity from each other have not been associated in data, such data have not been utilized for enlargement of the dynamic range.

However, the coordinate of data is measured accurately whereby coordinate data with high accuracy can be added to information of foreign matter. By making use of such coordinate data, even detection in the plurality of foreign matter detection systems different from each other, the continuity of foreign matter is judged to provide a wide dynamic range. The coordinate data processed by different processing system are associated to make use for enlargement of dynamic range.

In a preferred typical embodiment of the present invention, there comprises a light source section for emitting a first luminous flux and a second luminous flux irradiated on the surface of an inspected object; a first irradiation optical system in which the first luminous flux is irradiated on the surface of an inspected object at a first irradiation angle; a second irradiation optical system in which the second luminous flux is irradiated on the surface of an inspected object at a second irradiation angle different from the first irradiation angle; a displacement section for relatively displacing an inspected object and an irradiation luminous flux of the irradiation optical system; a light receiving optical system for receiving scattered light of the first luminous flux irradiated by the first irradiation optical system and produced from an inspection object on the surface of an inspected object and scattered light of the second luminous flux irradiated by the second irradiation optical system and produced from an inspection object on the surface of an inspected object; a first light receiving section for converting scattered light of the first luminous flux received by the light receiving optical system into a first light receiving signal; a second light receiving section for converting scattered light of the second luminous flux received by the light receiving optical system into a second light receiving signal; and a signal forming section for forming a measuring signal on the basis of the first light receiving signal and the second light receiving signal. The first light receiving section and the second light receiving section form a first light receiving signal and a second light receiving signal which are different in dynamic range from each other. The signal forming section synthesizes the first light receiving signal and the second light receiving signal which are different in sensitivity or dynamic range from each other to form a measuring signal.

By the provision of such constitution as described, the dynamic range of the surface inspection apparatus can be enlarged by using a plurality of processing systems different in object or a plurality of processing systems different in sensitivity.

Preferably, the first characteristic of the first luminous flux emitted by the light source section and the second characteristic of the second luminous flux emitted by the light source section lie in wavelength of luminous flux or polarized-light component.

Preferably, the first irradiation angle of the first irradiation optical system is set to be smaller than the second irradiation angle of the second irradiation optical system.

Further, the light receiving optical system comprises a first light receiving optical system for receiving a first scattered light in a first scattering direction irradiated by the irradiation optical system and emitted from an inspection object on the surface of an inspected object, and a second light receiving optical system for receiving a second scattered light in a second scattering direction irradiated by the irradiation optical system and emitted from an inspection object on the surface of an inspected object. The first scattered light received by the first light receiving optical system is converted into a first light receiving signal by the first light receiving section, and the second scattered light received by the second light receiving optical system is converted into a second light receiving signal by the second light receiving section. The first light receiving signal and the second light receiving signal which are different in sensitivity or dynamic range from each other are synthesized to form a measuring signal by the signal forming section. In this case, various kinds of light source sections can be employed. For example, a light source section for emitting a single luminous flux will suffice.

Preferably, the first scattering direction is made so as to form a larger angle in an irradiating direction of the luminous flux than a second scattering direction.

Preferably, the signal forming section extracts a foreign matter signal included in the first light receiving signal and a foreign matter signal included in the second light receiving signal to discriminate that the foreign matter signal included in the fixed range in the respective right receiving signals results from the same foreign matter, and preferentially makes use of a light receiving signal on the side satisfied with the fixed condition to form a measuring signal.

Preferably, the signal forming section forms, in the first light receiving signal or the second light receiving signal, foreign matter data by a coordinate when crossing a fixed level and a peak level in the range exceeding the fixed level.

Preferably, the signal forming section forms, where a peak level is saturated when a foreign matter signal is detected by a light receiving signal of high sensitivity out of the first light receiving signal and the second receiving signal, foreign matter data on the basis of the light receiving signal of low sensitivity.

This invention has the following effects.

Even where devices different in sensitivity and devices arranged for different objects are used, a wide continuous dynamic range can be achieved. For example, a device is made so as to be regarded as the same coordinate system whereby a wide continuous dynamic range in a true sense according to the sensitivity of device with the coordinate data as a key can be achieved.

According to the present invention, a device of high sensitivity and a device of low sensitivity are combined whereby a small foreign matter to a large foreign matter can be measured to enable achievement of a wide dynamic range.

Since even by devices different in sensitivity and devices arranged for different objects, a wide continuous dynamic range can be achieved, there can be constructed a system capable of obtaining a continuous sensitivity caused by a combination of expensive devices and inexpensive devices.

Further, according to the present invention, the coordinate is measured with high accuracy whereby even data of processing systems different from each other and data obtained from detection systems different in sensitivity from each other, a dynamic range can be enlarged simply by using the measuring data having those data synthesized.

Therefore, expensive devices (for example, a photomultiplier or the like) can be used for a high sensitivity element, and inexpensive devices (for example, a photodiode or the like) can be used for a low sensitivity element. The combination of various kinds of devices as described is able to cope with various defects on small foreign matter corresponding to fineness, large foreign matter, and the surface of an inspected object by one measurement.

BRIEF DESCRIPTION OF THE DRAWINGS

The preferred embodiments of the present invention will be described with reference to the drawings.

DESCRIPTION OF THE PREFERRED EMBODIMENTS

Figure 1:
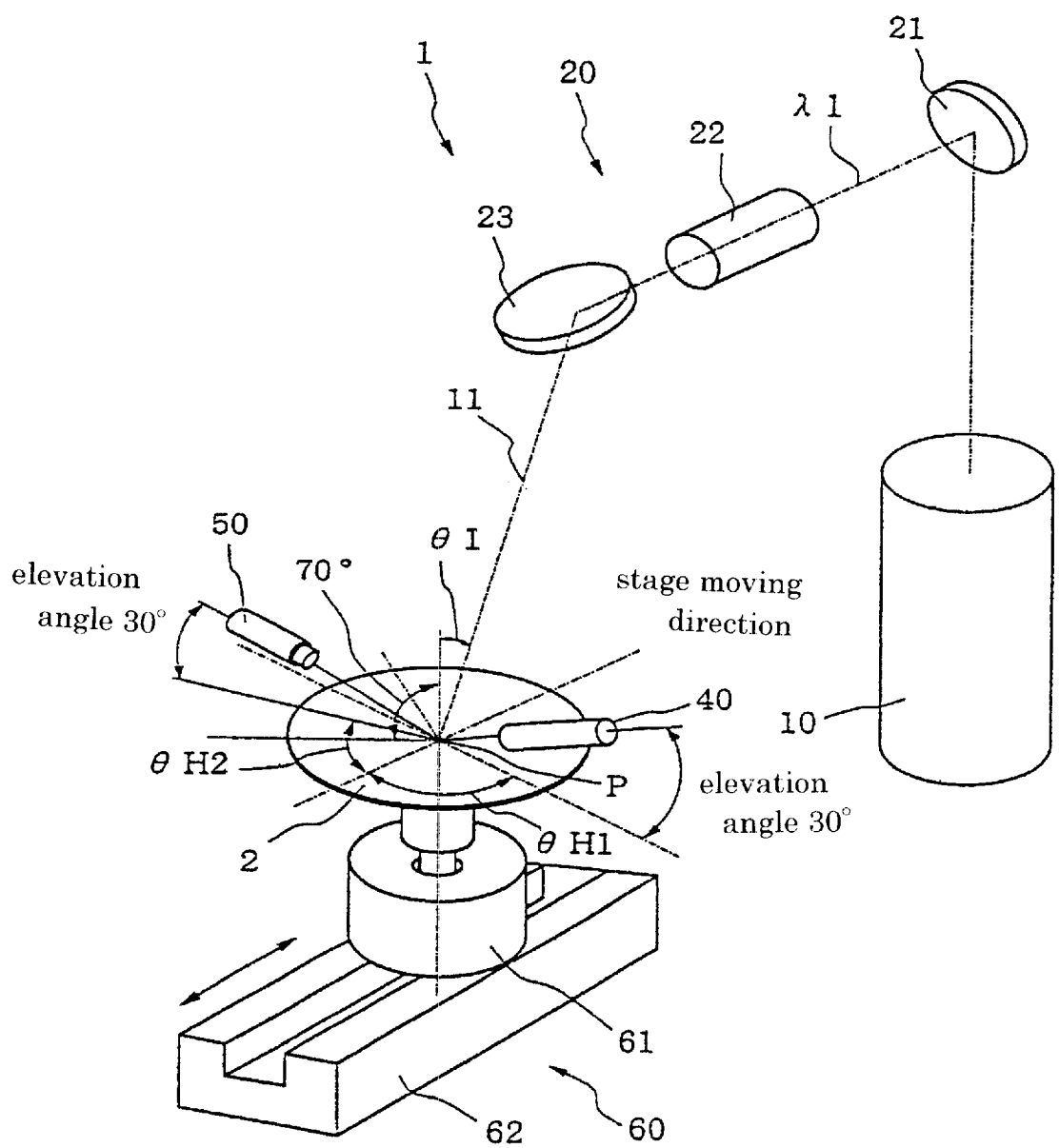
FIG. 1 is a schematic arrangement view of main optical elements of a surface inspection apparatus according to one embodiment of the present invention.

FIG. 1 is a schematic arrangement view of main optical elements of a surface inspection apparatus according to one preferred embodiment of the present invention.

A surface inspection apparatus 1 comprises a light source section 10 such as a laser tube for emitting a luminous flux 11 of at least wave length $\lambda$ 1, an irradiation optical system 20 for irradiating the luminous flux 11 of wavelength $\lambda$ 1 from the light source section 10 to a semiconductor wafer 2 as an inspected object at an irradiation angle $\theta$, a first light receiving optical system 40 for receiving scattered light from an inspection point P on the surface of the semiconductor wafer 2 caused by the luminous flux 11 irradiated by the irradiation optical system 20 in first scattering direction, a second light receiving optical system 50 for receiving scattered light from an inspection point P on the surface of the semiconductor wafer 2 caused by the luminous flux 11 irradiated by the irradiation optical system 20 in second scattering direction different from the first scattering direction, and a displacement section 60 for allowing the semiconductor wafer 2 as an inspected object to enable straight and rotational movement relatively with respect to the luminous flux 11 of the irradiation optical system 20. An angle of elevation of the first light receiving optical system 40 in the illustration is 30°.

The luminous flux 11 of wave length λ 1 emitted from the light source section 10 is changed in direction by a first mirror 21 so as to be irradiated on the irradiation point P on the surface of the semiconductor wafer 2 at an irradiation angle θ 1 through a group of first irradiation lenses 22 and a second mirror 23.

Where an inspected object, i.e., the foreign matter or the like is present at the irradiation point P, when the irradiation luminous flux is irradiated, scattered light occurs in accordance with the fixed directivity. The irradiation angle θ 1 is set as a reference of the normal direction of the inspected object 2. In the embodiment of FIG. 1, a fixed angle is selected for the irradiation angle θ 1.

The first light receiving optical system 40 (sidewise scattered light) and the second light receiving optical system 50 (forward scattered light) will be described hereinafter.

The first light receiving optical system 40 and the second light receiving optical system 50 are provided for receiving the aforementioned scattered light. The first light receiving optical system 40 receives the scattered light from the inspection point P on the surface of the semiconductor wafer 2 caused by the luminous flux 11 irradiated by the irradiation optical system 20 in the first scattering direction. The second light receiving optical system 50 receives the scattered light from the inspection point P on the surface of the semiconductor wafer 2 caused by the luminous flux 11 irradiated by the irradiation optical system 20 in the second scattering direction different from the first scattering direction.

A first light receiving horizontal angle θ H1 (for example, 90°) in the first scattering direction and a second light receiving horizontal angle θ H2 (for example, 50°) in the second scattering direction are measured as a reference of the reflecting direction when the irradiation luminous flux 11 caused by the irradiation optical system 20 is mirror-reflected by the inspected object 2. In the embodiment of FIG. 1, there is a relationship of the first light receiving horizontal angle θ H1>the second light receiving horizontal angle θ H2.

A light receiving elevation angle in the first and second light receiving directions is set, for example, to 30°.

Figure 2:
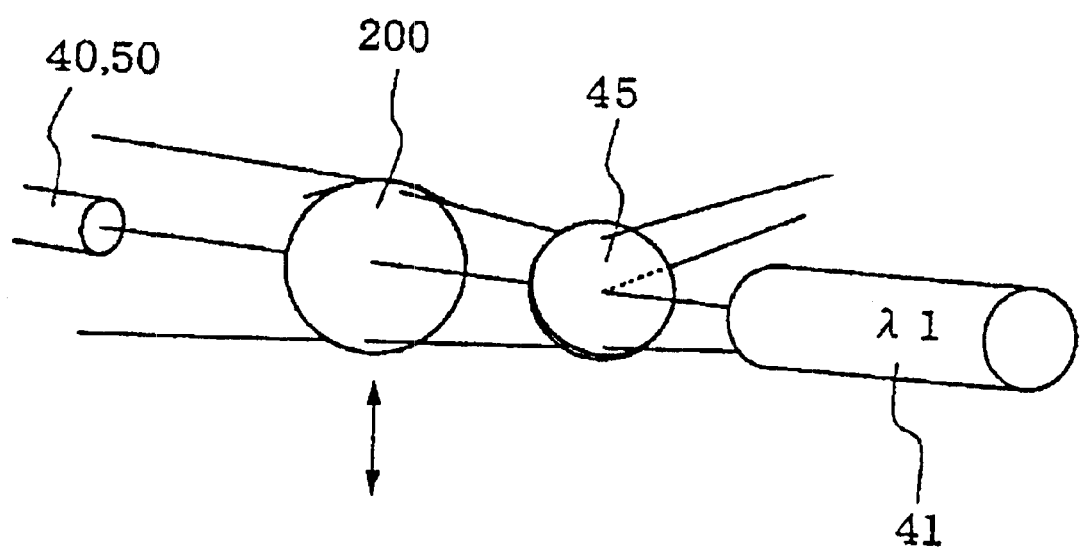
FIG. 2 is a detailed view of a light receiving optical system of the surface inspection apparatus according to the present invention.

As shown in FIG. 2, the received luminous flux received by the first light receiving optical system 40 is separated by a dichroic mirror 45 into luminous flux of wave length λ 1 via an ND filter 200 arranged movably in a direction of arrow (a vertical direction in FIG. 2) so that the luminous flux is inserted into or moved away from a light receiving optical path. A first light receiving section 41 receives scattered light of wave length λ 1 received by the first light receiving optical system 40 to convert it into a first light receiving signal.

Also in the second light receiving optical system 50, by the optical system similar to that shown in FIG. 2, the luminous flux is separated by the dichroic mirror 45 into luminous flux of first wave length λ 1 via the Neutral Density (ND) filter arranged movably in a direction of arrow (a vertical direction in FIG. 2). A second light receiving section 42 (as shown in FIG. 11) receives scattered light of first wave length λ 1 received by the second light receiving optical system 50 to convert it into a second light receiving signal.

Figure 11:
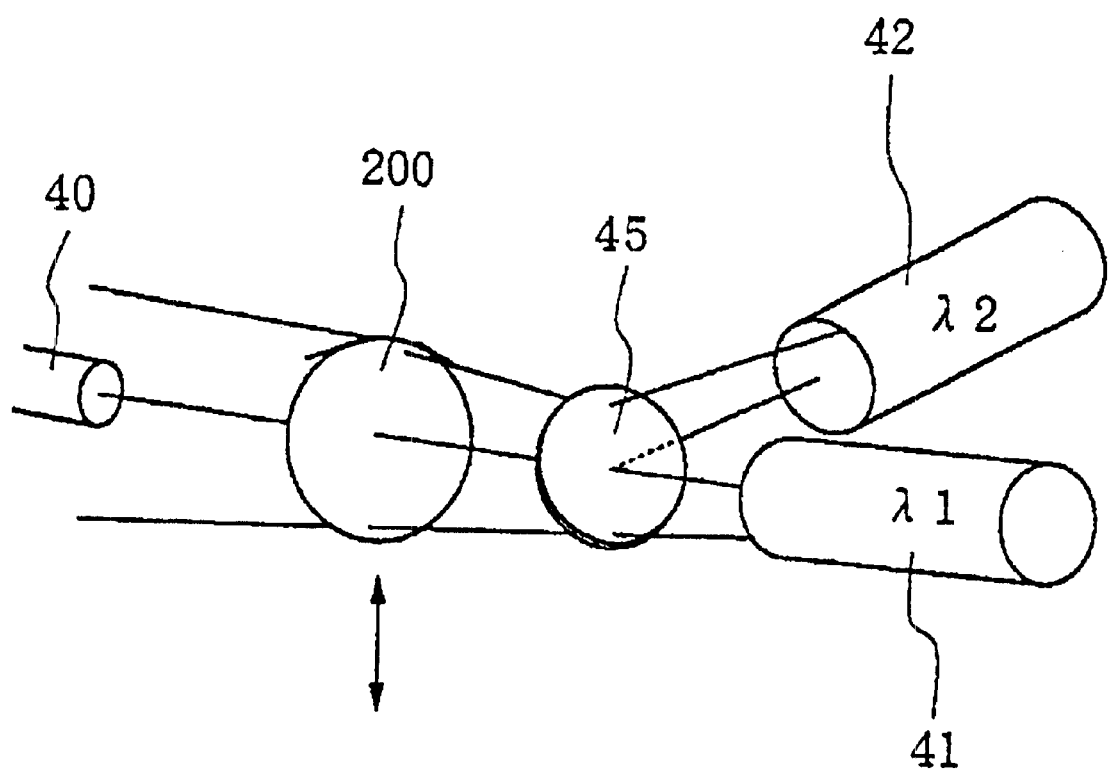
FIG. 11 is a detailed view of a light receiving optical system of the surface inspection apparatus shown in FIG. 10.

Preferably, the first light receiving section 41 and the second light receiving section 42 (as shown in FIG. 11) are light receiving elements such as a photomultiplier.

The displacement section 60 will now be described. The displacement section 60 comprises a rotation displacement section 61 for rotating and displacing an inspected object 2, and a straight-line displacement section 62 for straight-line displacing an inspected object 2. The straight-line displacement is merely moved at the fixed rate of the width of luminous flux with respect to displacement of one rotation of the rotation displacement section 61 to spirally scan the inspected object 2 throughout by irradiation light of the first irradiation optical system 20.

The present invention is not limited to the scanning method as described above, but the radiation luminous flux may be subjected to straight-line scanning by a polygon mirror or the like in place of the rotation displacement.

In the embodiment of FIG. 1, the rotation displacement section 61 comprises a rotation motor for rotating a rotation table, and the straight-line displacement section 62 comprises a slide movement section for moving the rotation motor linearly. The slide movement section causes, by movement thereof, an irradiation position of the irradiation luminous flux 11 of the irradiation optical system 20 to be displaced so as to pass through the center of the inspected object 2 to cross in a diametrical direction.

Figure 3:
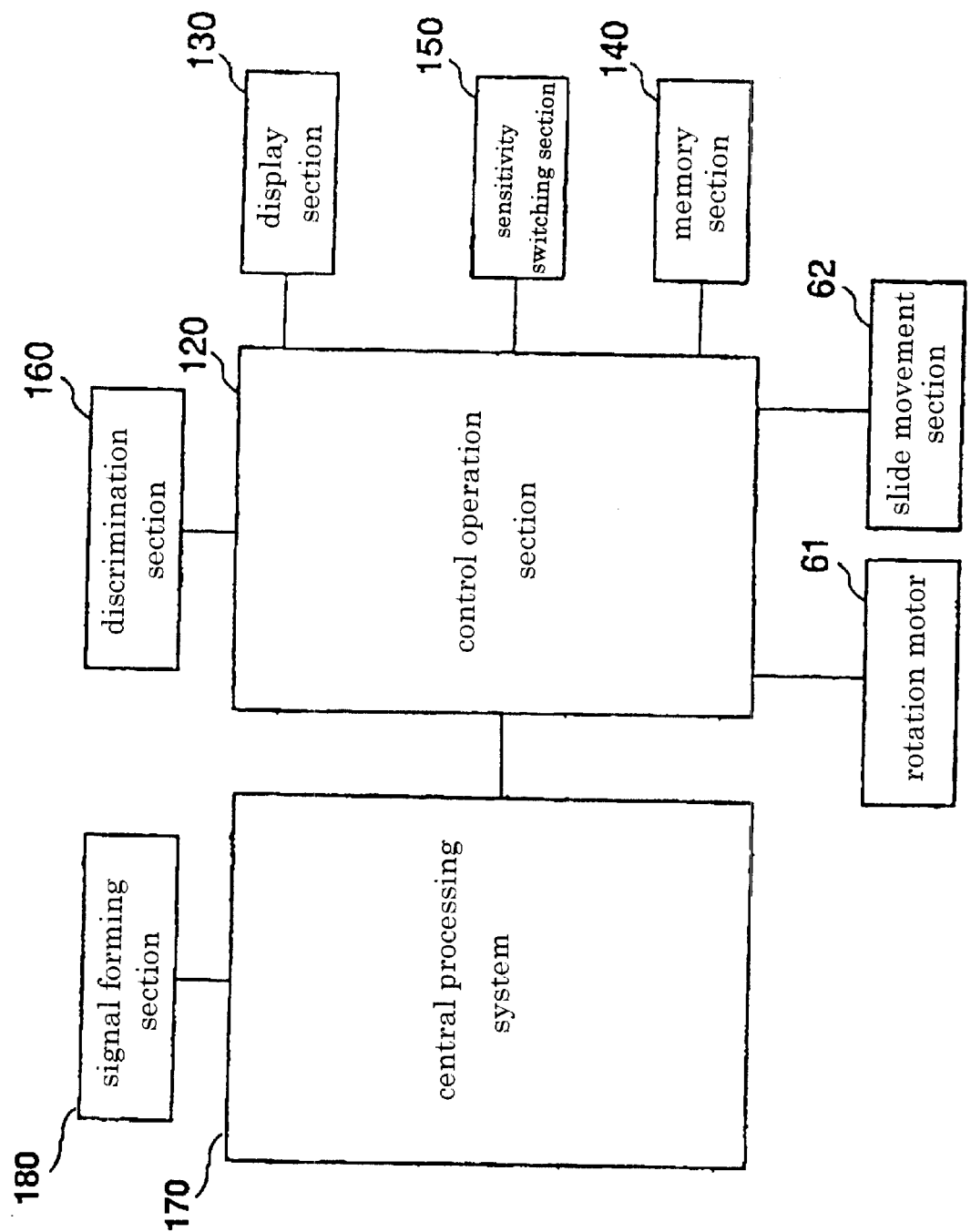
FIG. 3 is a block diagram of the surface inspection apparatus according to the present invention.

FIG. 3 is a block diagram of the surface inspection apparatus according to the present invention.

A measuring signal is fed from a central processing system 170 described later to a control operation section 120 for carrying out function of a signal processing section to effect fixed signal processing. The control operation section 120 carries out fixed signal processing to display the inspection result on a display section 130 as necessary, to store it in a memory section 140, or to read the stored content.

The control operation section 120 controls a discrimination section 160. The discrimination section 160 discriminates a kind of inspection objects on an inspected object.

Further, the control operation section 120 controls the rotation motor of the rotation displacement section 61 and the slide movement section of the straight-line displacement section 62, or controls a sensitivity switching section 150 of the first light receiving section 41 and the second light receiving section 42 (as shown in FIG. 11).

The sensitivity switching section 150 carries out sensitivity switching by moving the ND filter 200 in a direction of arrow in FIG. 2, and inserting the ND filter 200 into the light receiving windows of the first light receiving section 41 and the second light receiving section 42 (as shown in FIG. 11) to lower the sensitivity, or moving the ND filter 200 away from the light receiving window to raise the sensitivity.

When the first light receiving section 41 and the second light receiving section 42 (as shown in FIG. 11) are formed from a photomultiplier, the sensitivity can be also switched by regulating a voltage applied thereto.

Figure 4:
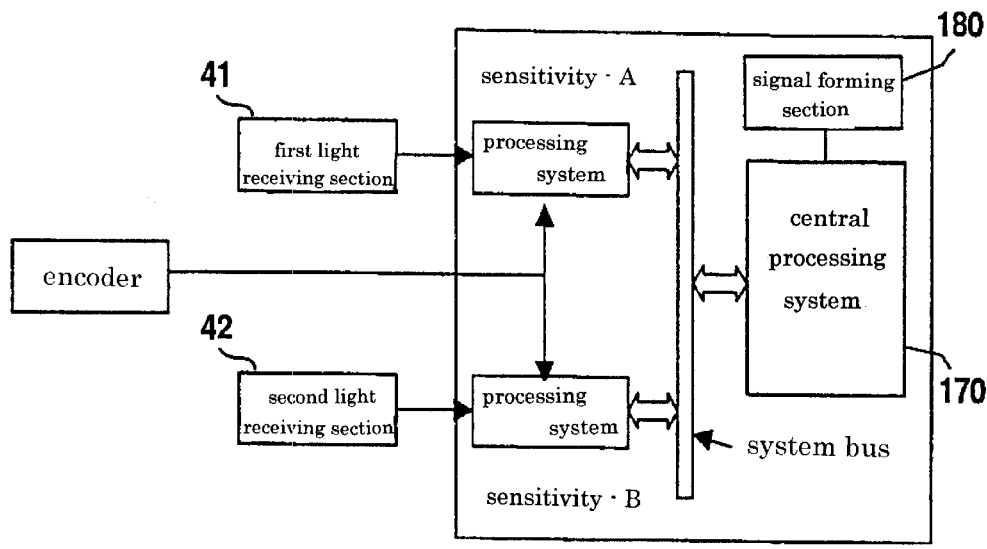
FIG. 4 is a block diagram of a system for forming a measuring signal by a central processing system of the surface inspection apparatus according to the present invention.

FIG. 4 is a block diagram of a system for forming a measuring signal by the central processing system.

The first scattered light received by the first light receiving optical system 40 is converted into a first light receiving signal by the first light receiving section 41. The first light receiving signal is subjected to fixed signal processing described later by a processing system on the sensitivity A side. Here, the sensitivity A is a high sensitivity system. The first light receiving signal subjected to the signal processing is stored in a memory section within the processing system on the sensitivity A side.

The second scattered light received by the second light receiving optical system 50 is converted into the second light receiving signal by the second light receiving section 42. The second light receiving signal is subjected to fixed signal processing described later by the processing system on the sensitivity B side. Here, the sensitivity B is a low sensitivity system. The second light receiving signal subjected to the signal processing is stored in a memory section within the processing system on the sensitivity B side.

The processing system on the sensitivity A side and the processing system on the sensitivity B side are independent from each other.

The first light receiving section 41 and the second light receiving section 42 provide different sensitivities by making adjustment (changing a gain or the like). The first light receiving section 41 and the second light receiving section 42 may use devices of different kind.

A measuring signal is formed by a signal forming section 180 of the central processing system 170 on the basis of a first light receiving signal processed on the sensitivity A side and a second light receiving signal processed on the sensitivity B side described previously.

Figure 5:
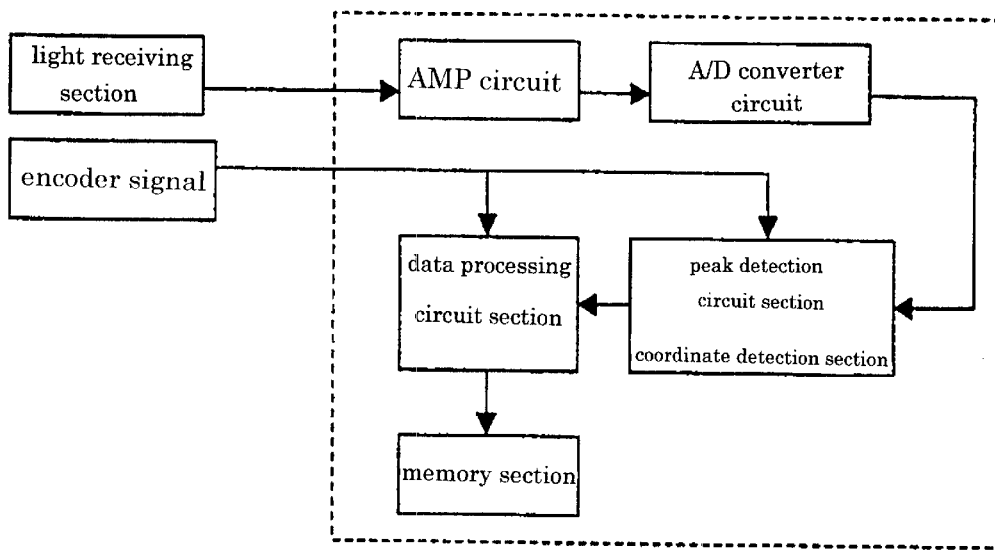
FIG. 5 is a block diagram of the processing system shown in FIG. 4.

FIG. 5 is a block diagram showing one example of the processing system shown in FIG. 4.

The first light receiving signal or the second light receiving signal is fed to an A/D converter circuit through an AMP circuit within the processing system from the light receiving section. The light receiving signal is converted from an analog signal into a digital signal by the A/D converter circuit, which is fed to a peak detection circuit section and a coordinate detection section. In the peak detection circuit section and the coordinate detection section, foreign matter data are extracted by an encoder signal. The foreign matter data are subjected to fixed data processing by the data processing circuit section. Then, the foreign matter data is stored in the memory section. The foreign matter data comprises four elements of a start coordinate, a peak coordinate, an end coordinate and a peak level value.

Figure 6:
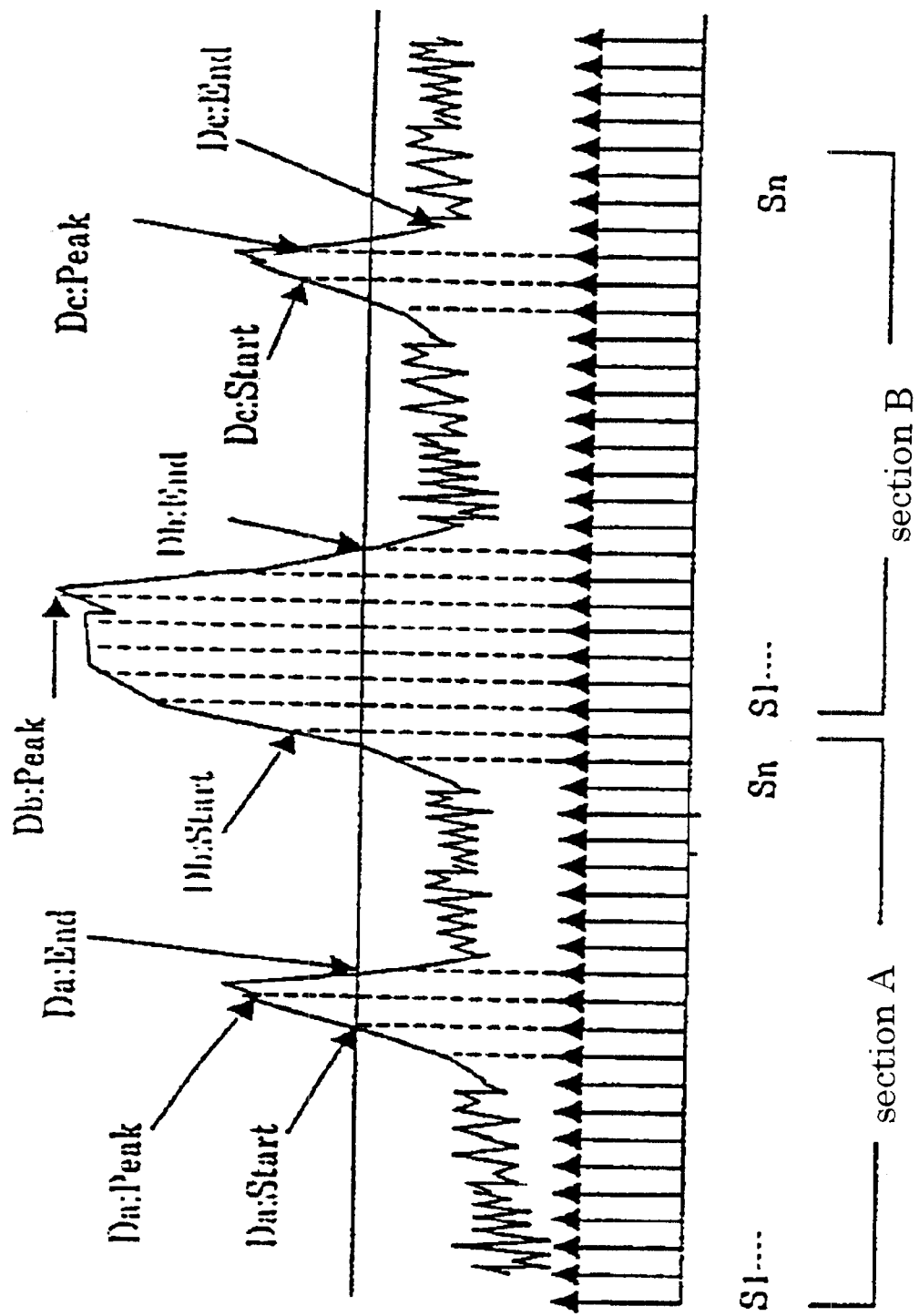
FIG. 6 is a view showing the construction of inspection object data in a light receiving signal according to the surface inspection apparatus of the present invention.
Figure 7:
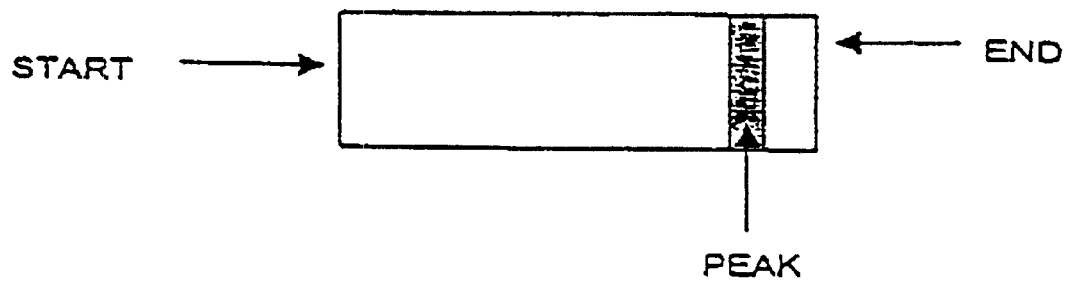
FIG. 7 is a schematic view showing one example of the inspection object data according to the surface inspection apparatus of the present invention.

FIG. 6 is a view showing one example of the construction of foreign matter data in the light receiving signal. FIG. 7 is a schematic view of foreign matter data as described.

In scanning detection light in a fixed direction, when a scattered signal of foreign matter exceeds a threshold signal (shown by the solid line horizontally in FIG. 6), that is stored as a start coordinate (Start), and afterward, when the scattered signal of foreign matter lowers than the threshold signal, that is stored as an end coordinate (End), whereby that where the scattered signal of foreign matter between the start coordinate and the end coordinate is highest is stored as a peak level value (Peak). Foreign matter on the surface of an inspected object is specified on the basis of foreign matter data comprising a start coordinate (Start), a peak level value (Peak), and an end coordinate (End).

In FIG. 6, since foreign matters Da, Db and Dc are specified, the number of foreign matters is three. In this case, data between sections A and B has nothing to do with the number of foreign matter, and three is counted as the number of foreign matter. With respect to data of foreign matter Da, the start coordinate is Da:Start, the peak level value is Da Peak, and the end coordinate is Da:End. Data of other foreign matters are also the same.

The central processing system shown in FIG. 4 will be further explained.

The central processing system 170 seeks for data having a peak level value saturated from the first light receiving signal stored in the memory section (FIG. 5) on the sensitivity A side to obtain a coordinate thereof. The central processing system 170 retrieves data of the second light receiving signal stored in the memory section (FIG. 5) on the sensitivity B side on the basis of the data coordinate having its peak level value saturated. At that time, the succeeding processing is done. A fixed range about the data coordinate having a peak level value saturated is retrieved on the sensitivity B side. Where foreign matter is detected in the fixed range on the sensitivity B side, the foreign matter is judged to be the same foreign matter as that detected as data saturated on the sensitivity A side.

On the sensitivity B side, the fixed continuity of foreign matter detected is judged. Foreign matter having the fixed continuity on the sensitivity B side is regarded as one continuous foreign matter. Such a one continuous foreign matter is judged to be the same foreign matter as that detected as saturated data on the sensitivity A side. Where data is saturated on the sensitivity A side as described above, data on the sensitivity B side is employed in the coordinate where the saturated data is positioned. The size of foreign matter is obtained from data obtained on the sensitivity A side or on the sensitivity B side.

The central processing system 170 further seeks for data having a peak level value saturated from the first light receiving signal stored in the memory section (FIG. 5) on the sensitivity A side, and carries out processing similar to that mentioned above.

As described above, the central processing system 170 further applies processing with respect to the first light receiving signal and the second light receiving signal processed by the processing systems which are independent from each other. And, the central processing system 170 forms a measuring signal in the signal forming section 180. The signal forming section 180 preferentially makes use of a light receiving signal (here, the first light receiving signal) on the high sensitivity side to synthesize the first light receiving signal and the second light receiving signal to form a measuring signal. Further, the signal forming section 180 forms foreign data on the basis of the light receiving signal (the first light receiving signal) on the high sensitivity side and the light receiving signal (the second light receiving signal) on the low sensitivity side.

Figure 8:
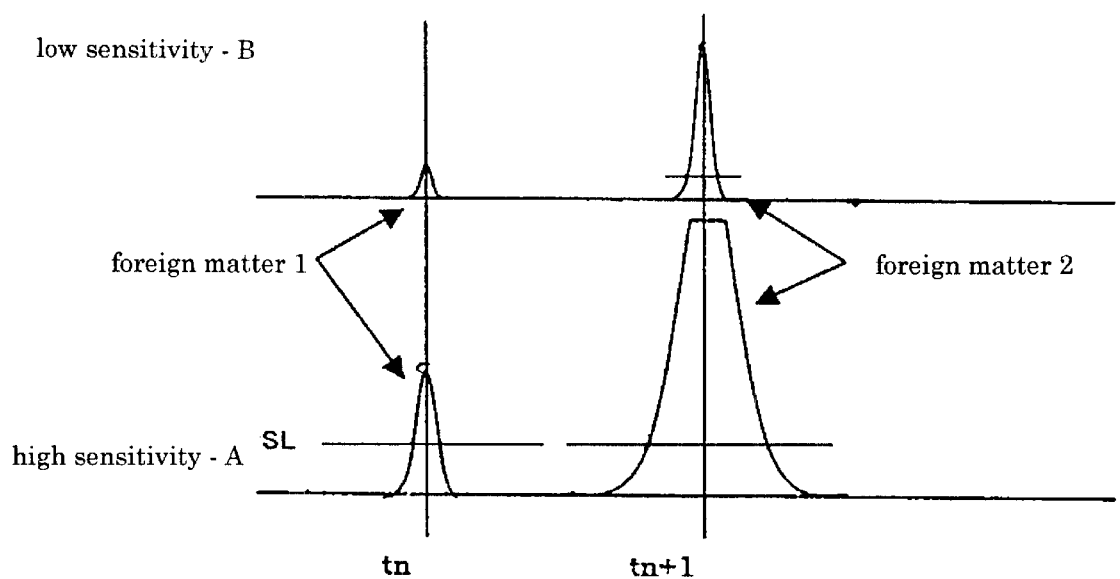
FIG. 8 is a view showing one example of the light receiving signal according to the surface inspection apparatus of the present invention.

For example, where a light receiving signal as shown in FIG. 8 is obtained, foreign matter 1 and foreign matter 2 are recognized on the high sensitivity side A.

Since the foreign matter 2 is saturated on the sensitivity A side, there seeks for data on the sensitivity B side in the same coordinate as that of data saturated on the sensitivity A side. In a coordinate $t_{n+1}$, data on the sensitivity B side is employed. In this case, coordinate data is expressed by time t. A signal to be a reference of a coordinate position normally makes use of a common signal, but in case of a high speed clock, preferably, signals different from each other are used.

In case of FIG. 8, in the sensitivity B, even if the foreign matter 1 and the foreign matter 2 are recognized, only the foreign matter 2 will be an object, and data of the sensitivity B is employed for data having the size of the foreign matter 2.

As described above, the central processing system forms a measuring signal at the signal forming section on the basis of data obtained on the sensitivity A side and on the sensitivity B side.

Figure 9:
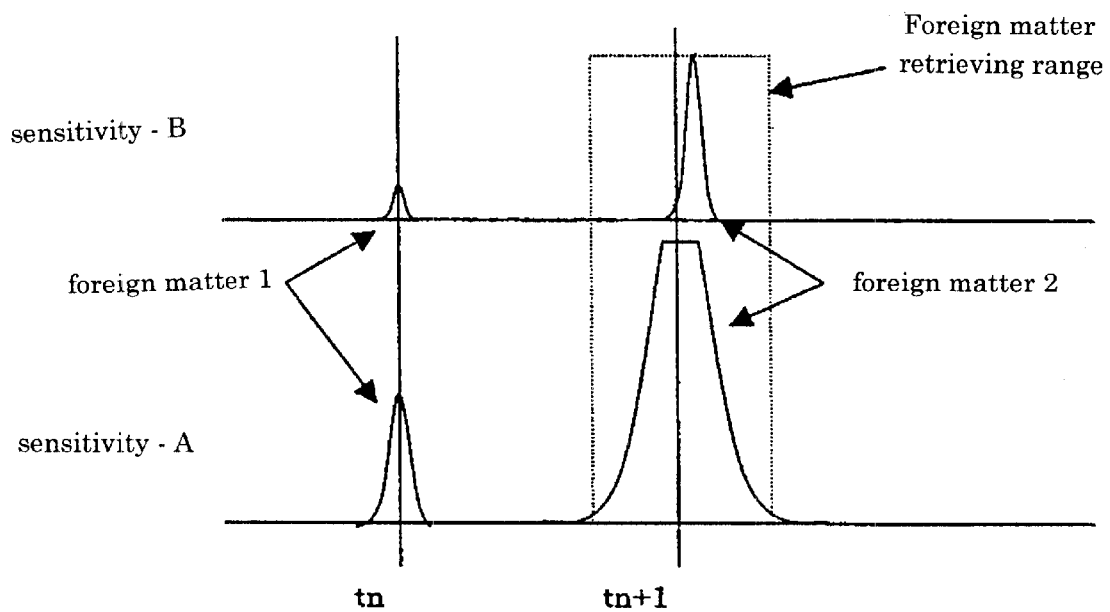
FIG. 9 is a view showing one example of the light receiving signal according to the surface inspection apparatus of the present invention.

For example, where a light receiving signal as shown in FIG. 9 is obtained, foreign matter 1 and foreign matter 2 are recognized in the sensitivity A. Since the foreign matter 2 is saturated on the sensitivity A side, there seeks for data on the sensitivity B side having the same coordinate as that of data saturated on the sensitivity A side. In a coordinate $t_{n+1}$, data on the sensitivity B side is employed. In this case, coordinate data is expressed by time t. In this case, even if the foreign matter 2 is not coincided in time $t_{n+1}$ between the sensitivity A side and the sensitivity B side but where data is not present in the surroundings, a fixed range on the sensitivity B side is retrieved to recognize the foreign matter 2 on the sensitivity B side as the foreign matter on the sensitivity A side. The fixed range as described may be a range at the skirt of the foreign matter 2 on the sensitivity A side or a range in consideration of a time error or a coordinate error in the measuring system.

As described above, in the central processing system, a measuring signal is formed in the signal forming section on the basis of data obtained on the sensitivity A side and on the sensitivity B side.

As described above, the formed measuring signal is fed to the control operation section 120 for the fixed signal processing.

Figure 10:
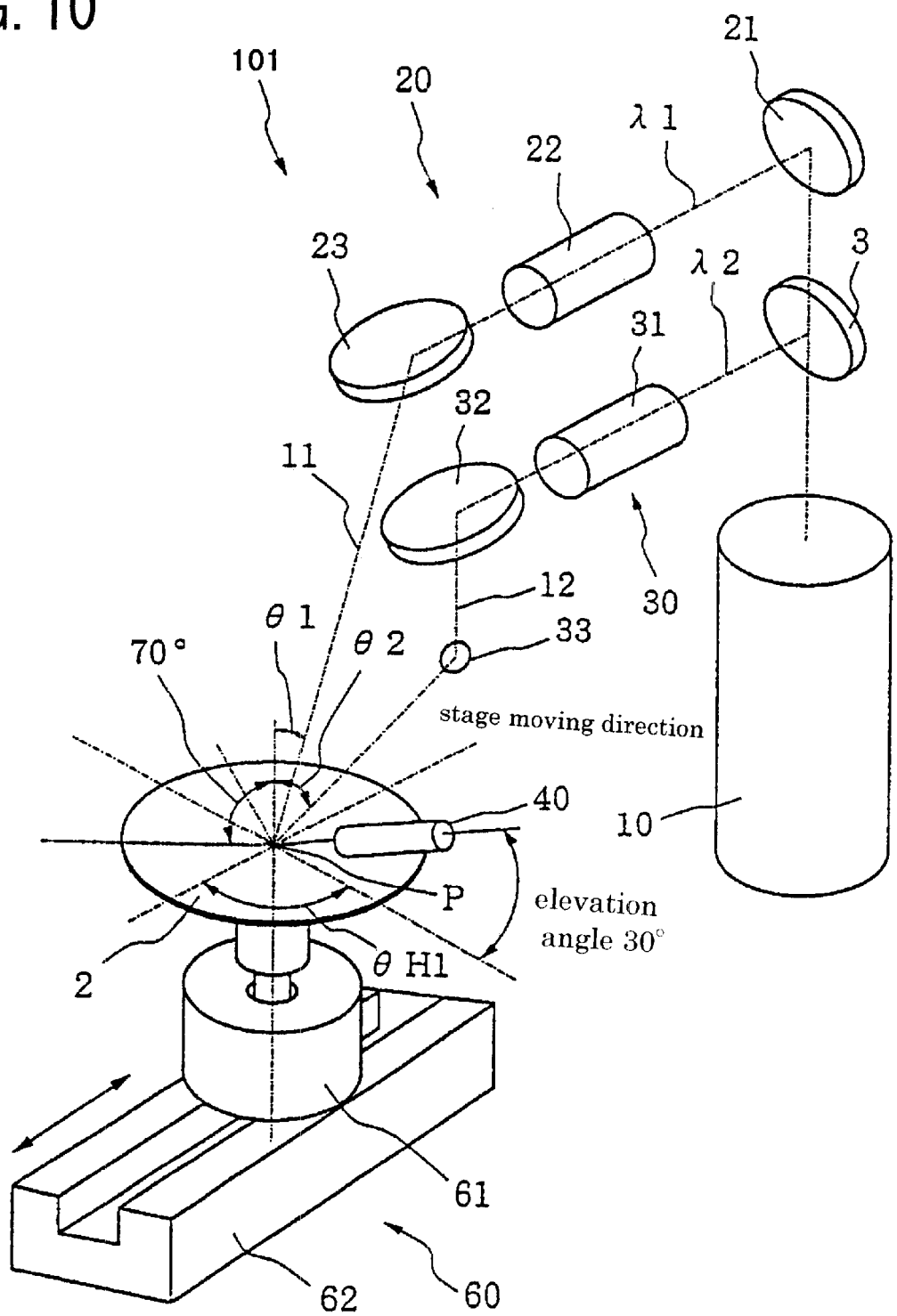
FIG. 10 is a view showing a modified embodiment of the surface inspection apparatus of the present invention.

FIG. 10 is a view showing a modified embodiment of the surface inspection apparatus according to the present invention.

In FIG. 10, a surface inspection apparatus 101 comprises a light source section 10 such as a laser tube for emitting a luminous flux 11 of at least a first wave length λ 1 and a luminous flux 12 of a second wave length λ 2 different from the former, a first irradiation optical system 20 for irradiating the luminous flux 11 of the first wavelength λ 1 from the light source section 10 to a semiconductor wafer 2 as an inspected object at a first irradiation angle θ 1, a second irradiation optical system 30 for irradiating the luminous flux 12 of the second wavelength λ 2 from the light source section 10 to an inspection point P on the surface of a semiconductor wafer 2 at a second irradiation angle θ 2 similarly to the first irradiation optical system 10, a first light receiving optical system 40 for receiving scattered light from the inspection point P on the surface of the semiconductor wafer 2 caused by the luminous fluxes 11 and 12 irradiated by the first irradiation optical system 20 and the second irradiation optical system 30 in a first light receiving direction, and a displacement section 60 for allowing the semiconductor wafer 2 as an inspected object to enable straight and rotational movement relatively with respect to the irradiation luminous flux 11 of the first irradiation optical system 20. An angle of elevation of the first light receiving optical system 40 of FIG. 10 is 30°.

The light source section 10 will be described. As the light source section 10 for emitting at least the luminous flux 11 of a first wavelength and the luminous flux 12 of a second wavelength different therefrom, various sources for emitting luminous fluxes of a plurality of wavelengths can be used. For example, employment can be made of a configuration in which luminous fluxed of a plurality of wavelengths are emitted by a single light source such as a multi-line laser, and a configuration in which luminous fluxed of a plurality of light sources for emitting a luminous flux of different wavelength are synthesized to form a single beam by a half mirror or the like.

Where in employing a multi-line laser, a luminous flux of unnecessary wavelength occurs, only the luminous flux of necessary wavelength can be taken out by causing it to pass through a band pass filter passing through the first wavelength and the second wavelength.

Where a plurality of light sources for emitting luminous fluxes of different wavelength are used, a plurality of luminous fluxes are synthesized by a half mirror or the like to form a single beam.

Where an argon ion laser is used as the light source section 10 in FIG. 10, preferably, a wavelength of 488 nm and a wavelength of 514.5 nm are selected. With respect to a luminous flux emitted from the light source section 10, a diachronic mirror 3 for causing the luminous flux 11 of a first wavelength λ 1, and reflecting the luminous flux 12 of a second wavelength λ 2 is used whereby the luminous flux 11 of a first wavelength and the luminous flux 12 of a second wavelength are separated. The luminous flux 11 of a first wavelength is changed in direction by a first mirror 21, and is irradiated on an irradiation point P on the surface of an inspected object 2 at a first irradiation angle θ 1 through a group of first irradiation lenses 22 and a second mirror 23. The luminous flux 12 of a second wavelength is reflected by a dichroic mirror 3, and is irradiated on an irradiation point P on the surface of an inspected object 2 at a second irradiation angle θ 2 through a group of second irradiation lenses 31, a third mirror 32, and a fourth mirror 33.

Where an inspected object, that is, foreign matter is present on the irradiation point P, when an irradiation luminous flux is irradiated thereon, scattered light occurs in accordance with the fixed directivity. The first irradiation angle θ 1 and the second irradiation angle θ 2 are set with a normal direction of an inspected object 2 as a reference. In the embodiment of FIG. 10, for the first irradiation angle θ 1, a fixed angle is selected from the range of 0 to 40 degrees as an incident angle. For the second irradiation angle θ 2, a fixed angle is selected from the range of 50 to 85 degrees. The horizontal direction may be coincided or different.

In the embodiment of FIG. 10, a relationship of the first irradiation angle θ 1<the second irradiation angle θ 2 is established. The size of the first wavelength λ 1 and the second wavelength λ 2 can be optionally selected. However, there is the tendency that the greater the incident angle, the better the detection sensitivity, and the shorter the using wavelength λ, the better the detection sensitivity. Therefore, if a relationship in which the second wavelength λ 2 is shorter than the first wavelength λ 1 (the first wavelength λ 1>the second wavelength λ 2) is present, it can be set in a direction that the detection sensitivity caused by the first irradiation angle θ 1 is equal to the detection sensitivity caused by the second irradiation angle θ 2.

Next, the first light receiving optical system 40 will be described.

The first light receiving optical system 40 is provided for receiving the aforementioned scattered light. The first light receiving optical system 40 receives, in a first light receiving direction, scattered light from the inspection point P on the surface of the semiconductor wafer 2 caused by the luminous fluxes 11, 12 irradiated by the first irradiation optical system 20 and the second irradiation optical system 30.

A first light receiving horizontal angle θ H1 (for example 90°) in the first light receiving direction is measured with a reflecting direction, as a reference, when the irradiation luminous fluxes 11, 12 caused by the first irradiation optical system 20 or the second irradiation optical system 30 are mirror-reflected by the inspected object 2. The light receiving elevation angle in the first light receiving direction is set, for example, to 30°.

As shown in FIG. 11, the received luminous flux received by the first light receiving optical system 40 is separated by a second dichroic mirror 45 into luminous flux of a first wavelength λ 1 and luminous flux of a second wavelength λ 2 via an ND filter 200 arranged movably in a direction of arrow so that the flux is inserted into or moved away from a light receiving optical path. A first light receiving section 41 receives scattered light of a first wave length λ 1 received by the first light receiving optical system 40 to convert it into a first light receiving signal. The second light receiving section 42 receives scattered light of a second wave length λ 2 received by the first light receiving optical system 40 to convert it into a second light receiving signal. Preferably, the first light receiving section 41 and the second light receiving section 42 are light receiving elements such as a photomultiplier.

The displacement section 60 will now be described. The displacement section 60 comprises a rotation displacement section 61 for rotating and displacing an inspected object 2, and a straight-line displacement section 62 for straight-line displacing an inspected object 2. The straight-line displacement is merely moved at the fixed rate of the width of luminous flux with respect to displacement of one rotation of the rotation displacement section 61 to spirally scan the inspected object 2 throughout by irradiation light of the first and second irradiation optical systems 20, 30.

The present invention is not limited to the scanning method as described above. For example, the irradiation luminous flux may be subjected to straight-line scanning by a polygon mirror or the like in place of the rotation displacement.

In the embodiment of FIG. 10, the rotation displacement section 61 comprises a rotation motor for rotating a rotation table, and the straight-line displacement section 62 comprises a slide movement section for moving the rotation motor linearly. The slide movement section causes, by movement thereof, irradiation positions of the irradiation luminous fluxes 11, 12 of the irradiation optical systems 20, 30 to be displaced so as to pass through the center of the inspected object 2 to cross in a diametrical direction.

Figure 12:
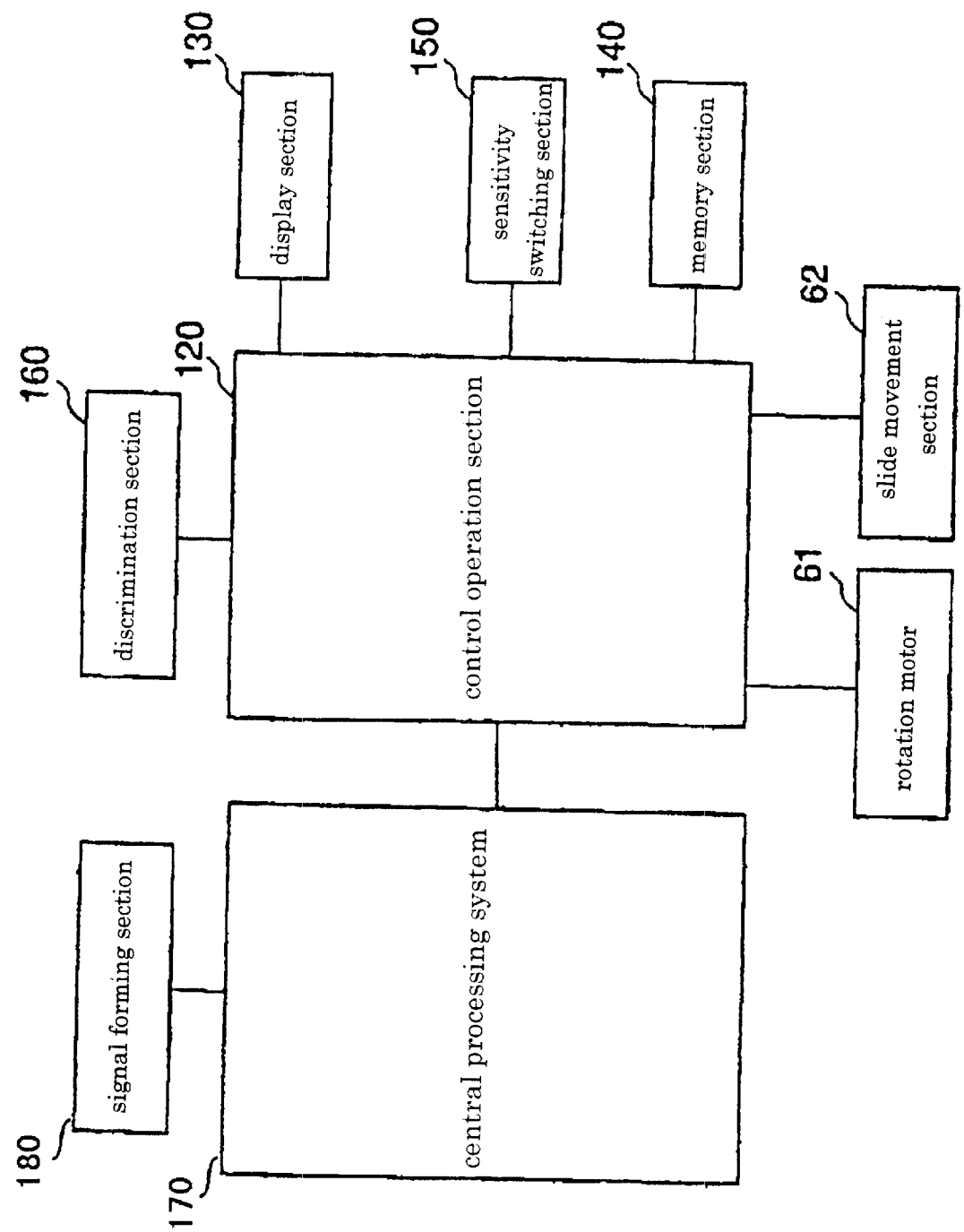
FIG. 12 is a block diagram of the surface inspection apparatus shown in FIG. 10.

FIG. 12 is a block diagram of the surface inspection apparatus shown in FIG. 10.

A measuring signal is fed from a central processing system 170 described later to a control operation section 120 for carrying out function of a signal processing section to effect fixed signal processing. The control operation section 120 carries out selecting light receiving signals described later and fixed signal processing to display the inspection result on a display section 130 as necessary, to store it in a memory section 140, or to read the stored content.

The control operation section 120 controls a discrimination section 160. The discrimination section 160 discriminates a kind of inspection objects on an inspected object.

Further, the control operation section 120 controls a rotation motor of the rotation displacement section 61 and the slide movement section of the straight-line displacement section 62, or controls a sensitivity switching section 150 of the first light receiving section 41 and the second light receiving section 42.

The sensitivity switching section 150 carries out sensitivity switching by moving the ND filter 200 in a direction of arrow in FIG. 2, and inserting the ND filter 200 into the light receiving windows of the first light receiving section 41 and the second light receiving section 42 to lower the sensitivity, or moving the ND filter 200 away from the light receiving window to raise the sensitivity.

When the first light receiving section 41 and the second light receiving section 42 are formed from a photomultiplier, the sensitivity can be also switched by regulating a voltage applied thereto.

Next, formation of a measuring signal in the case where two luminous fluxes different in wavelength from each other, are irradiated at incident angles different from each other will be described.

Figure 13:
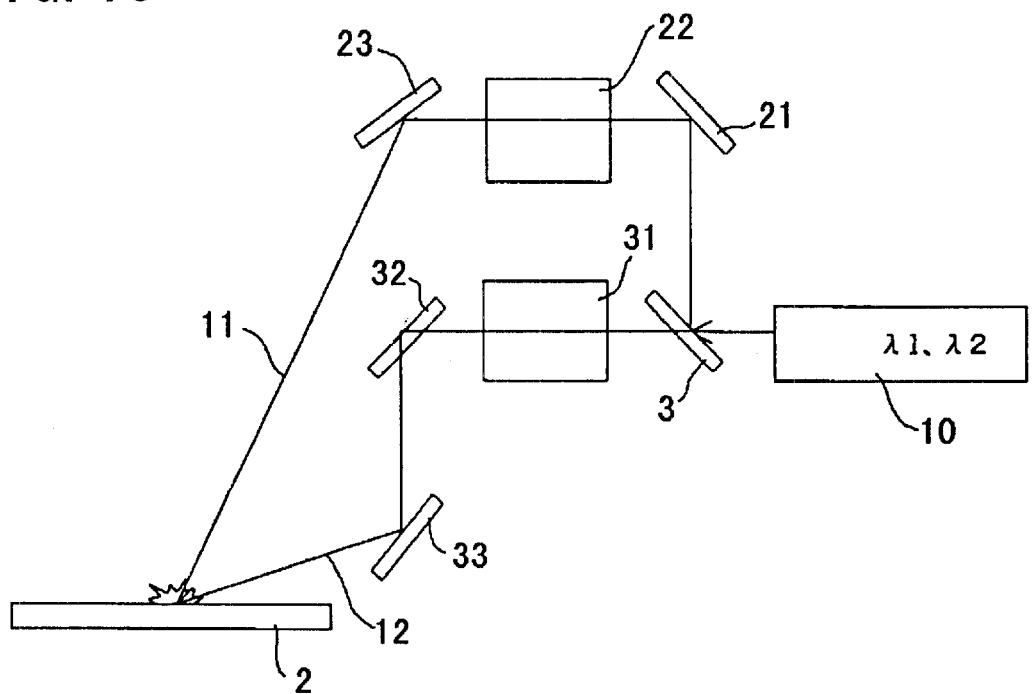
FIG. 13 is a schematic block diagram of a projection system of the surface inspection apparatus shown in FIG. 10.

FIG. 13 is a schematic block diagram showing a projection system of the surface inspection apparatus shown in FIG. 10.

Figure 14:
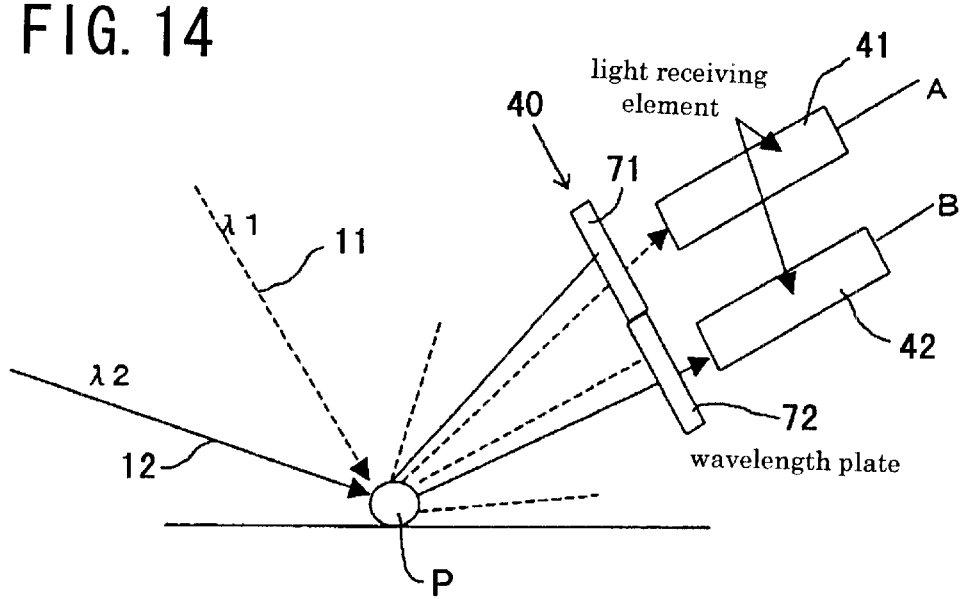
FIG. 14 is a block diagram of a detection light receiving system of the surface inspection apparatus shown in FIG. 10.

As shown in FIG. 13, the first luminous flux 11 of wavelength λ 1 and the second luminous flux 12 of wavelength λ 2 are irradiated on the surface of the inspected object. Then, as shown in FIG. 14, when the first luminous flux 11 of wavelength λ 1 and the second luminous flux 12 of wavelength λ 2 are irradiated on the foreign matter P on the surface of the inspected object, scattered light occurs from the foreign matter P. The scattered light is received by the light receiving optical system 40. The light receiving optical system 40 has a first wavelength plate 71 for causing scattered light of the first luminous flux 11 of wavelength λ 1 to pass through and a second wavelength plate 72 for causing scattered light of the second luminous flux 12 of wavelength λ 2 to pass through. The scattered light caused by the first luminous flux 11 of wavelength λ 1 passes through the first wavelength plate 71 and does not pass through the second wavelength plate 72. The scattered light caused by the second luminous flux 12 of wavelength λ 2 passes through the second wavelength plate 72 and does not pass through the first wavelength plate 71.

The scattered light of the first luminous flux 11 received by the light receiving optical system 40 is converted into a first light receiving signal by a light receiving element (a first light receiving section) 41 on the sensitivity A side. The sensitivity A is set to a high sensitivity. The scattered light of the second luminous flux 12 received by the light receiving optical system 40 is converted into a second light receiving signal by a light receiving element (a second light receiving section) 42 on the sensitivity B side. The sensitivity B is set to a low sensitivity.

It is noted that the first light receiving section and the second light receiving section belong to detection systems different in magnification from each other. The detection systems different in magnification from each other have sensitivity different from each other. The first light receiving section and the second light receiving section may use devices different in kind.

The systems having magnification different from each other are subjected to calibration by Polystyrene latex (PSL) particles adjusting to the respective sensitivities. At that time, one or more at minimum calibration with the same particles is (are) adjusted between the systems different from each other.

Figure 15:
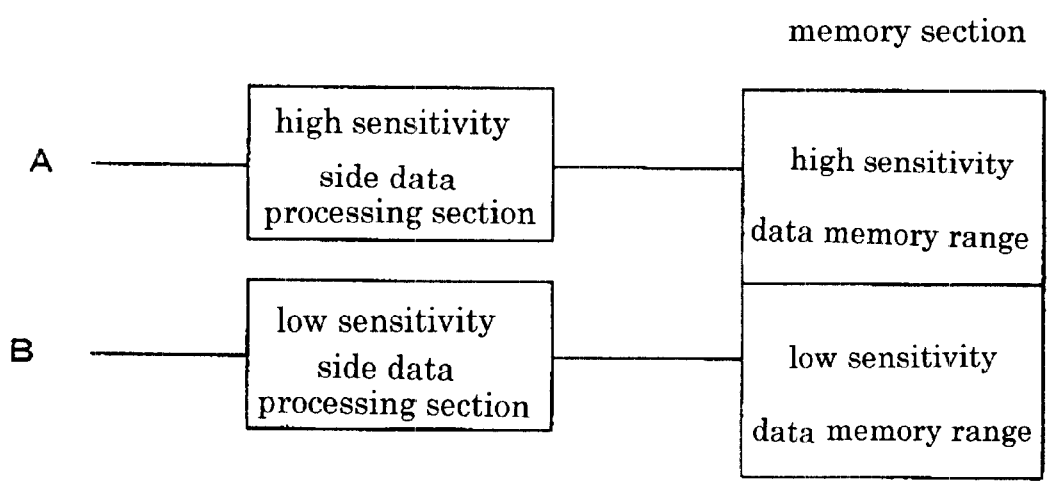
FIG. 15 is a block diagram showing a processing system and a memory section of the surface inspection apparatus shown in FIG. 10.

FIG. 15 is a block diagram showing a processing system and a memory section in the surface inspection apparatus shown in FIG. 10.

In FIG. 15, a first light receiving signal is subjected to fixed data processing by a high sensitivity side data processing section (processing system). The first light receiving signal subjected to the data processing is stored as high sensitivity side scattered data in the high sensitivity data memory range of the memory section. The first light receiving signal has the X coordinate and Y coordinate, scattered strength, Z information, foreign matter shape, detection size, and other information. The second light receiving signal is subjected to fixed data processing by a low sensitivity side data processing section (processing system). The second light receiving signal subjected to the data processing is stored as low sensitivity side scattered data in the low sensitivity data memory range of the memory section. The second light receiving signal has the X coordinate and Y coordinate, scattered strength, Z information, foreign matter shape, detection size, and other information.

The high sensitivity side data processing section and the low sensitivity side data processing section are independent from each other as shown in FIG. 15.

A measuring signal is formed in the signal forming section of the central processing system on the basis of the first light receiving signal processed on the sensitivity A side and the second light receiving signal processed on the sensitivity B side.

Figure 16:
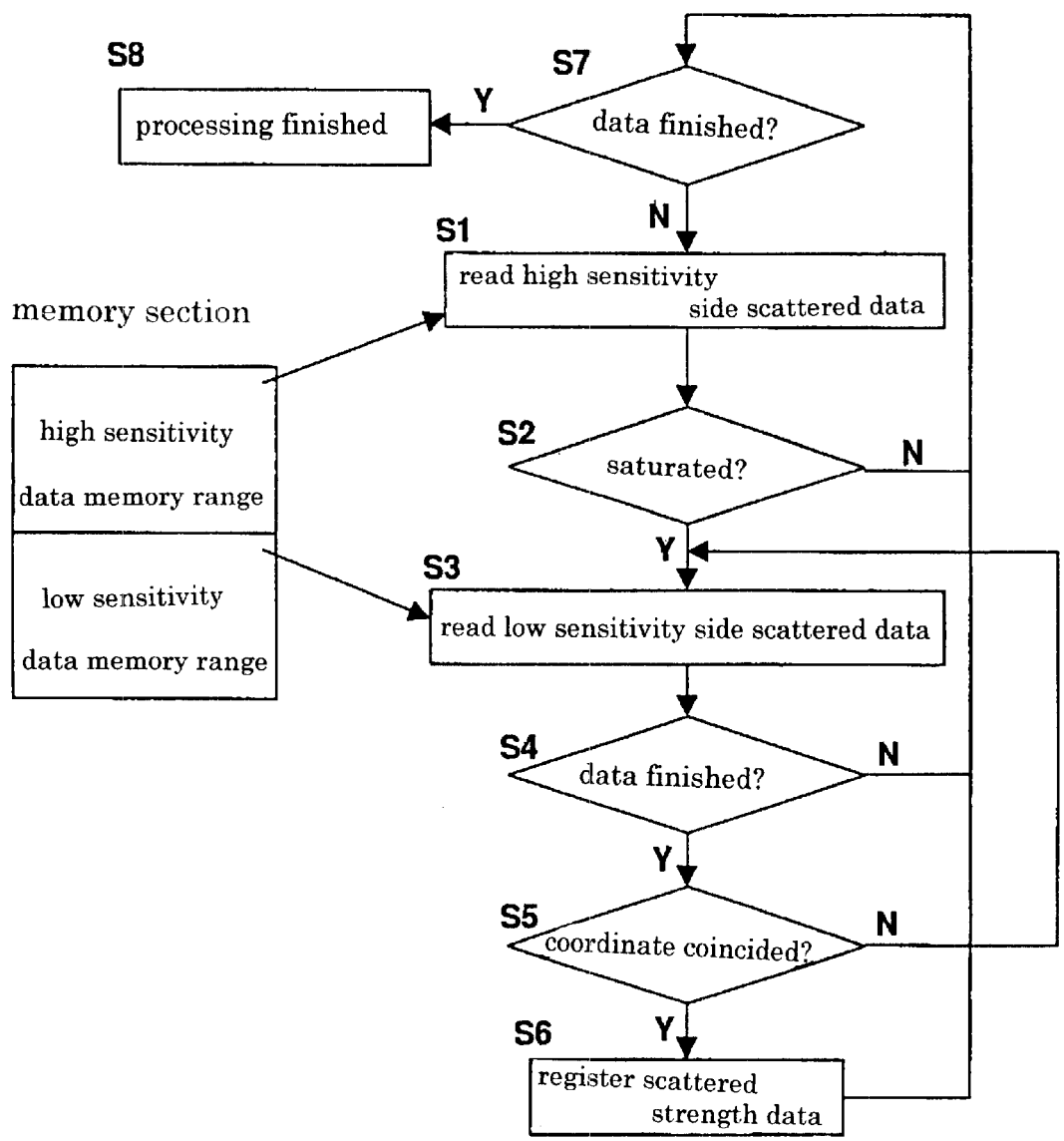
FIG. 16 is a flow chart view showing the measuring signal forming process by the central processing system of the surface inspection apparatus shown in FIG. 10.

FIG. 16 is a flow chart of the measuring signal forming processing by the central processing system.

The central processing system processes the high sensitivity side scattered data and the low sensitivity side scattered data stored in the memory section to form a measuring signal, according to the processing procedures of FIG. 16.

This will be described hereinafter in order. First, the central processing system read high sensitivity side scattered data (a first light receiving signal) from the high sensitivity data memory range. Then, the procedure proceeds to Step S2 to judge whether or not the read high sensitivity side scattered data (a first light receiving signal) is saturated. If the high sensitivity side scattered data is saturated, that is, if the high sensitivity side scattered data is saturated data, the procedure proceeds to Step S3. If in Step S2, the high sensitivity side scattered data is not saturated, the procedure proceeds to Step S7 described later to judge whether or not the high sensitivity side scattered data to be further processed is present. If the high sensitivity side scattered data is saturated, this means that the high sensitivity side scattered data exceeds an upper limit slice of the high sensitivity.

In Step S3, the low sensitivity data memory range is retrieved in the fixed retrieving range with a coordinate in which the saturated high sensitivity side scattered data is positioned as a reference. The fixed retrieving range with a coordinate in which the scattered high sensitivity side scattered data is positioned as a reference is determined in advance as the retrieving condition. Then, the low sensitivity side scattered data is read, the procedure proceeds to Step S4. In Step S4, judgment is made whether or not one data of foreign matter contained in the low sensitivity side scattered data had been read in the midst of reading the low sensitivity side scattered data. After one data of foreign matter contained in the low sensitivity side scattered data had been read in the midst of reading the low sensitivity side scattered data, the procedure proceeds to Step S5. Where one data of foreign matter contained in the low sensitivity side scattered data had not yet been read in the midst of reading the low sensitivity side scattered data, the procedure proceeds to Step S3 to continue reading.

In Step S5, when the coordinate of the low sensitivity side scattered data read in the fixed retrieving range is within the fixed range from the coordinate of the saturated high sensitivity side scattered data with as a reference for determining the retrieving range, the coordinate of the low sensitivity side scattered data is regarded to have coincided with the coordinate of the high sensitivity side scattered data, and the procedure proceeds to Step S6. When the coordinate of the low sensitivity side scattered data read in the fixed retrieving range is not present within the fixed range from the coordinate of the saturated high sensitivity side scattered data with as a reference for determining the retrieving range, the procedure proceeds to Step S3. In Step S3, the low sensitivity side scattered data is further read, and reads data of next foreign matter contained in the low sensitivity side scattered data in the fixed retrieving range determined as the retrieving condition. Then, the procedures similar to those mentioned above are repeated.

In Step S6, the scattered strength and detection size of data of foreign matter contained in the low sensitivity side scattered data to have been regarded to have coincided with the coordinate of the saturated high sensitivity side scattered data are registered in data as the scattered strength and detection size of a measuring signal in the coordinate thereof. Subsequently, the procedure proceeds to Step S7.

In Step S7, judgment is made whether or not reading of the high sensitivity side scattered data has been finished. If it had been read, the procedure proceeds to Step S8. Formation of a measuring signal is finished. Where reading has not been finished, the procedure proceeds to Step S1 to continue reading of the high sensitivity side scattered data. The procedures similar to those mentioned above are repeated.

The present invention is not limited to the above-described embodiments.

In modifications, data may be detected by respective detection systems, and data may be processed by processing systems corresponding to the respective detection systems. At that time, measuring may be carried out by irradiating twice the luminous fluxes having the same wavelength on the surface of the inspected object at angles different from each other. In this case, in two times of irradiation of luminous flux, measuring is carried out using a common light receiving element. The detection system may not have a function of selecting wavelengths.

Further, in a further modification, incident light may be attenuated, for example, by an ND filter or the like so that the magnifications of the detection systems are made to be different from each other.

What is claimed is:

1. A surface inspection apparatus comprising:
   a light source section for emitting a first luminous flux and a second luminous flux irradiated on a surface of an inspected object;
   a first irradiation optical system in which the first luminous flux is irradiated on the surface of the inspected object at a first irradiation angle;
   a second irradiation optical system in which the second luminous flux is radiated on the surface of the inspected object at a second irradiation angle different from the first irradiation angle;
   a displacement section for displacing the inspected object relative to irradiation luminous fluxes of the first and second irradiation optical systems;
   a light receiving optical system for receiving scattered light of the first luminous flux irradiated by the first irradiation optical system and produced from an inspection object on the surface of the inspected object and scattered light of the second luminous flux irradiated by the second irradiation optical system and produced from the inspection object on the surface of the inspected object;
   a first light receiving section for converting scattered light of the first luminous flux received by the light receiving optical system into a first light receiving signal;

a second light receiving section for converting scattered light of the second luminous flux received by the light receiving optical system into a second light receiving signal; and a signal forming section for forming a measuring signal on the basis of the first light receiving signal and the second light receiving signal, wherein the first light receiving section and the second light receiving section respectively form the first light receiving signal and the second light receiving signal which are different in sensitivity or dynamic range from each other, wherein the signal forming section synthesizes the first light receiving signal and the second light receiving signal which are different in sensitivity or dynamic range from each other to form the measuring signal, and wherein the signal forming section forms foreign matter data on the basis of the first light receiving signal at a high sensitivity side when both the first and second light receiving signals are not saturated, and forms foreign matter data on the basis of the first light receiving signal at a low sensitivity side when only one of the first and second light receiving signals is saturated.

2. A surface inspection apparatus according to claim 1, wherein a first characteristic of the first luminous flux emitted by the light source section and a second characteristic of the second luminous flux emitted by the light source section lie in a wavelength of luminous flux or polarized-light component.

3. A surface inspection apparatus according to claim 1, wherein a first irradiation angle of the first irradiation optical system is set to be smaller than a second irradiation angle of the second irradiation optical system.

4. A surface inspection apparatus comprising:

a light source section for emitting a luminous flux irradiated on a surface of an inspected object;

an irradiation optical system for irradiating a luminous flux on the surface of the inspected object at a fixed irradiation angle;

a displacement section for displacing the inspected object relative to an irradiation luminous flux of the irradiation optical system;

a first light receiving optical system for receiving a first scattered light in a first scattering direction of the irradiation luminous flux irradiated by the irradiation optical system and emitted from an inspection object on the surface of the inspected object;

a second light receiving optical system for receiving a second scattered light in a second scattering direction of the irradiation luminous flux irradiated by the irradiation optical system and emitted from the inspection object on the surface of the inspected object;

a first light receiving section for converting the first scattered light received by the first light receiving optical system into a first light receiving signal;

a second light receiving section for converting the second scattered light received by the second light receiving optical system into a second light receiving signal; and a signal forming section for synthesizing the first light receiving signal and the second light receiving signal to thereby form a measuring signal, wherein the first light receiving section and the second light receiving section respectively form the first light receiving signal and the second light receiving signal which are different in sensitivity or dynamic range from each other, wherein the signal forming section synthesizes the first light receiving signal and the second light receiving signal which are different in sensitivity or dynamic range to form the measuring signal, and wherein the signal forming section forms foreign matter data on the basis of the first light receiving signal at a high sensitivity side when both the first and second light receiving signals are not saturated, and forms foreign matter data on the basis of the first light receiving signal at a low sensitivity side when only one of the first and second light receiving signals is saturated.

5. A surface inspection apparatus according to claim 4, wherein a first scattering direction forms a larger angle with respect to the irradiation direction of luminous flux than that of a second scattering direction.

6. A surface inspection apparatus according to claim 4, wherein the signal forming section extracts a foreign matter signal included in the first light receiving signal and a foreign matter signal included in second light receiving signal, to discriminate that the foreign matter signals included in a predetermined range in respective light receiving signals so that the light receiving signals which are satisfied with predetermined conditions are used preferentially to form the measuring signal.

7. A surface inspection apparatus according to claim 6, wherein the signal forming section forms foreign matter data by a start coordinate and an end coordinate when crossing a fixed level and by a peak coordinate and a peak level in a range between the start coordinate and the end coordinate exceeding the fixed level on the basis of the first light receiving signal or the second light receiving signal.

8. A surface inspection apparatus according to claim 7, wherein the signal forming section forms foreign matter data on the basis of the light receiving signal lower in sensitivity, when the foreign matter signal that is detected by the light receiving signal higher in sensitivity out of the first light receiving signal and the second light receiving signal is saturated.

9. A surface inspection apparatus comprising:

a light emitting means for emitting a first luminous flux and a second luminous flux for irradiating on a surface of an inspected object;

a first irradiation means for irradiating the first luminous flux on the surface of the inspected object at a first irradiation angle;

a second irradiation means for irradiating the second luminous flux on the surface of the inspected object at a second irradiation angle different from the first irradiation angle;

a displacement means for displacing the inspected object relative to irradiation luminous fluxes of the first and second irradiation means;

a light receiving means for receiving scattered light of the first luminous flux irradiated by the first irradiation means and produced from an inspection object on the surface of the inspected object, and scattered light of the second luminous flux irradiated by the second irradiation means and produced from the inspection object on the surface of the inspected object;

a first conversion means for converting scattered light of the first luminous flux received by the light receiving means into a first light receiving signal;

a second conversion means for converting scattered light of the second luminous flux received by the light receiving means into a second light receiving signal;

a signal forming means for forming a measuring signal on the basis of the first light receiving signal and the second light receiving signal, wherein the first conversion means and the second conversion means respectively form the first light receiving signal and the second light receiving signal which are different in sensitivity or dynamic range from each other, wherein the signal forming means synthesizes the first light receiving signal and the second light receiving signal which are different in sensitivity or dynamic range from each other to form the measuring signal, and wherein the signal forming means forms foreign matter data on the basis of the first light receiving signal at a high sensitivity side when both the first and second light receiving signals are not saturated, and forms foreign matter data on the basis of the first light receiving signal at a low sensitivity side when only one of the first and second light receiving signals is saturated.

10. A surface inspection apparatus according to claim 9, wherein the light emitting means includes a first light emitting unit and a second light emitting unit, and wherein a first characteristic of the first luminous flux emitted by the first light emitting unit and a second characteristic of the second luminous flux emitted by the second light emitting unit lie in a wavelength of luminous flux or polarized-light component.

11. A surface inspection apparatus according to claim 9, wherein a first irradiation angle of the first irradiation means is set to be smaller than a second irradiation angle of the second irradiation optical system.

12. A surface inspection apparatus comprising:

a light emitting means for emitting a luminous flux for irradiating on a surface of an inspected object;

an irradiation means for irradiating a luminous flux on the surface of the inspected object at a fixed irradiation angle;

a displacement means for displacing the inspected object relative to an irradiation luminous flux of the irradiation means;

a first light receiving means for receiving a first scattered light in a first scattering direction of the irradiation luminous flux irradiated by the irradiation means and produced from an inspection object on the surface of the inspected object;

a second light receiving means for receiving a second scattered light in a second scattering direction of the irradiation luminous flux irradiated by the irradiation means and produced from the inspection object on the surface of the inspected object;

a first conversion means for converting the first scattered light received by the first light receiving means into a first light receiving signal;

a second conversion means for converting the second scattered light received by the second light receiving means into a second light receiving signal;

a signal forming means for forming a measuring signal by synthesizing the first light receiving signal and the second light receiving signal, wherein the first conversion means and the second conversion means respectively form the first light receiving signal and the second light receiving signal which are different in sensitivity or dynamic range from each other, wherein the signal forming means forms the measuring signal by synthesizing the first light receiving signal and the second light receiving signal which are different in sensitivity or dynamic range from each other, and wherein the signal forming means forms foreign matter data on the basis of the first light receiving signal at a high sensitivity side when both the first and second light receiving signals are not saturated, and forms foreign matter data on the basis of the first light receiving signal at a low sensitivity side when only one of the first and second light receiving signals is saturated.

13. A surface inspection apparatus according to claim 12, wherein the first scattering direction forms a larger angle with respect to the irradiation direction of luminous flux than that of the second scattering direction.

14. A surface inspection apparatus according to claim 12, wherein the signal forming means extracts a foreign matter signal included in the first light receiving signal and a foreign matter signal included in the second light receiving signal, to discriminate that the foreign matter signals included in a predetermined range in respective light receiving signals so that the light receiving signals which are satisfied with predetermined conditions are used preferentially to form the measuring signal.

15. A surface inspection apparatus according to claim 14, wherein the signal forming means forms foreign matter data by a start coordinate and an end coordinate when crossing a fixed level and by a peak coordinate and a peak level in a range between the start coordinate and the end coordinate exceeding the fixed level on the basis of the first light receiving signal or the second light receiving signal.

16. A surface inspection apparatus according to claim 15, wherein the signal forming means forms foreign matter data in the basis of the light receiving signal of low sensitivity, when the foreign matter signal detected by the light receiving signal that is higher in sensitivity out of the first light receiving signal and the second light receiving signal is saturated.

17. A surface inspection method comprising:

a step for emitting a first luminous flux and a second luminous flux for irradiating on a surface of an inspected object;

a step for irradiating the first luminous flux on the surface of the inspected object at a first irradiation angle;

a step for irradiating the second luminous flux on the surface of the inspected object at a second irradiation angle different from the first irradiation angle;

a step for displacing the inspected object relative to an irradiation luminous flux;

a step for receiving scattered light of the first luminous flux produced from an inspection object on the surface of the inspected object, and scattered light of the second luminous flux produced from the inspection object on the surface of the inspected object;

a step for converting the scattered light of the received first luminous flux into a first light receiving signal;

a step for converting the scattered light of the received second luminous flux into a second light receiving signal; and a step for forming a measuring signal on the basis of the first light receiving signal and the second light receiving signal, wherein in the conversion step into the first light receiving signal and the conversion step into the second light receiving signal, the first light receiving signal and the second light receiving signal which are different in sensitivity or dynamic range from each other are formed, wherein in the signal forming step, the first light receiving signal and the second light receiving signal which are different in sensitivity or dynamic range from each other are synthesized to form the measuring signal, and wherein the signal forming step forms foreign matter data on the basis of the first light receiving signal at a high sensitivity side when both the first and second light receiving signals are not saturated, and forms foreign matter data on the basis of the first light receiving signal at a low sensitivity side when only one of the first and second light receiving signals is saturated.

18. A surface inspection method according to claim 17, wherein a first characteristic of the first luminous flux and a second characteristic of the second luminous flux are a wavelength of luminous flux or a polarized-light component.

19. A surface inspection method according to claim 17, wherein the first irradiation angle in the irradiation step of the first luminous flux is set to be smaller than that of the second irradiation angle in the irradiation step of the second luminous flux.

20. A surface inspection method comprising:

a step for emitting a luminous flux for irradiating on a surface of an inspected object;

a step for irradiating a luminous flux on the surface of the inspected object at a fixed irradiation angle;

a step for displacing the inspected object relative to an irradiation luminous flux;

a step for receiving a first scattered light in a first scattering direction produced from an inspection object on the surface of the inspected object;

a step for receiving a second scattered light in a second scattering direction produced from the inspection object on the surface of the inspected object;

a step for converting the received first scattered light into a first light receiving signal;

a step for converting the received second scattered light into a second light receiving signal; and a step for forming a measuring signal by synthesizing the first light receiving signal and the second light receiving signal, wherein in the conversion step into the first light receiving signal and the conversion step into the second light receiving signal, the first light receiving signal and the second light receiving signal which are different in sensitivity or dynamic range from each other are formed, wherein in the signal forming step, the first light receiving signal and the second light receiving signal which are different in sensitivity or dynamic range from each other are synthesized to form the measuring signal, and wherein the signal forming section forms foreign matter data on the basis of the first light receiving signal at a high sensitivity side when both the first and second light receiving signals are not saturated, and forms foreign matter data on the basis of the first light receiving signal at a low sensitivity side when only one of the first and second light receiving signals is saturated.

21. A surface inspection method according to claim 20, wherein the first scattering direction forms a larger angle with respect to the irradiation direction of luminous flux than that of the second scattering direction.

22. A surface inspection method according to claim 20, wherein in the signal forming step, a foreign matter signal included in the first light receiving signal and a foreign matter signal included in the second light receiving signal are extracted, to discriminate that the foreign matter signals included in a predetermined range in respective light receiving signals so that the light receiving signals which are satisfied with predetermined conditions are used preferentially to form the measuring signal.

23. A surface inspection method according to claim 22, wherein the signal forming step forms foreign matter data by a start coordinate and an end coordinate when crossing a fixed level and by a peak coordinate and a peak level in a range between the start coordinate and the end coordinate exceeding the fixed level on the basis of the first light receiving signal or the second light receiving signal.

24. A surface inspection method according to claim 23, wherein, in the signal forming step, foreign matter data is formed on the basis of the light receiving signal of low sensitivity when the foreign matter signal detected from the light receiving signal of higher sensitivity out of the first light receiving signal and the second light receiving signal is saturated.

* * * * *